US007875036B2

(12) United States Patent
Burbank et al.

(10) Patent No.: US 7,875,036 B2
(45) Date of Patent: Jan. 25, 2011

(54) SHORT TERM TREATMENT FOR UTERINE DISORDER

(75) Inventors: Fred H. Burbank, Laguna Niguel, CA (US); Greig E. Altieri, Laguna Beach, CA (US); Michael L. Jones, San Clemente, CA (US); Ed Olson, Lake Forest, CA (US)

(73) Assignee: Vascular Control Systems, Inc., San Juan Capistrano, CA (US)

(*) Notice: Subject to any disclaimer, the term of this patent is extended or adjusted under 35 U.S.C. 154(b) by 1332 days.

(21) Appl. No.: 11/256,768

(22) Filed: Oct. 24, 2005

(65) Prior Publication Data

US 2006/0106109 A1     May 18, 2006

Related U.S. Application Data

(60) Provisional application No. 60/622,751, filed on Oct. 27, 2004.

(51) Int. Cl.
    *A61B 17/42*      (2006.01)
(52) U.S. Cl. ............................. 606/119; 606/205
(58) Field of Classification Search ................ 606/119, 606/205, 207, 208, 210, 211; 600/29, 135, 600/184, 196, 197, 220, 221, 225–228
See application file for complete search history.

(56) References Cited

U.S. PATENT DOCUMENTS

| 3,209,753 | A | 10/1965 | Hawkins et al. |
| 3,411,505 | A | 11/1968 | Nobis |
| 3,779,248 | A | 12/1973 | Karman |
| 4,120,302 | A | 10/1978 | Ziegler |
| 4,226,240 | A | 10/1980 | Walker |
| 4,292,960 | A | 10/1981 | Paglione |
| 4,428,374 | A | 1/1984 | Auburn |
| 4,428,379 | A | 1/1984 | Robbins et al. |
| 4,509,528 | A | 4/1985 | Sahota |

(Continued)

FOREIGN PATENT DOCUMENTS

DE     195 28 440 A     2/1997

(Continued)

OTHER PUBLICATIONS

Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.

(Continued)

*Primary Examiner*—Anhtuan T Nguyen
*Assistant Examiner*—Tuan V Nguyen (57) ABSTRACT

A method and device for treating a female patient's uterine disorder by occluding one or both of the patient's uterine artery. The treatment involves occluding one or both of the patient's uterine arteries with an intravaginal device to form a thrombus within the occluded artery or arteries and administering an agent which will prolong the occlusion of the artery or arteries after removal of the occluding device or initiate or accelerate fibroid cell apoptosis (programmed cell death). The intravaginal device has a pair of pivotally connected occluding members, with at least one of the occluding member having a movable occluding element on a distal shaft section of the occluding member.

13 Claims, 5 Drawing Sheets

U.S. PATENT DOCUMENTS

| | | |
|---|---|---|
| 4,650,466 A | 3/1987 | Luther |
| 4,757,823 A | 7/1988 | Hofmeister et al. |
| 4,945,896 A | 8/1990 | Gade |
| 4,991,588 A | 2/1991 | Pflueger et al. |
| 4,994,069 A | 2/1991 | Ritchart et al. |
| 5,037,433 A | 8/1991 | Wilk et al. |
| 5,081,997 A | 1/1992 | Bosley, Jr. et al. |
| 5,108,408 A | 4/1992 | Lally |
| 5,201,314 A | 4/1993 | Bosley et al. |
| 5,226,911 A | 7/1993 | Chee et al. |
| 5,261,409 A | 11/1993 | Dardel |
| 5,275,166 A | 1/1994 | Vaitenkunas et al. |
| 5,277,181 A | 1/1994 | Mendelson et al. |
| 5,289,831 A | 3/1994 | Bosley |
| 5,336,229 A | 8/1994 | Noda |
| 5,336,231 A | 8/1994 | Adair |
| 5,368,034 A | 11/1994 | Isner |
| 5,383,922 A | 1/1995 | Zipes et al. |
| 5,456,693 A | 10/1995 | Conston et al. |
| 5,458,596 A | 10/1995 | Lax et al. |
| 5,488,958 A | 2/1996 | Topel et al. |
| 5,496,331 A | 3/1996 | Xu et al. |
| 5,507,744 A | 4/1996 | Tay et al. |
| 5,542,944 A | 8/1996 | Bhatta |
| 5,549,624 A | 8/1996 | Mirigian et al. |
| 5,549,824 A | 8/1996 | Trumpf et al. |
| 5,556,396 A | 9/1996 | Cohen et al. |
| 5,562,680 A | 10/1996 | Hasson |
| 5,570,692 A | 11/1996 | Morinaga |
| 5,588,960 A | 12/1996 | Edwards et al. |
| 5,614,204 A | 3/1997 | Cochrum |
| 5,658,299 A | 8/1997 | Hart |
| 5,662,676 A | 9/1997 | Koninckx |
| 5,662,680 A | 9/1997 | Desai |
| 5,665,096 A | 9/1997 | Yoon |
| 5,672,153 A | 9/1997 | Lax et al. |
| 5,672,172 A | 9/1997 | Zupkas |
| 5,674,243 A | 10/1997 | Hale |
| 5,691,314 A | 11/1997 | Hodgen |
| 5,697,937 A | 12/1997 | Toma |
| 5,697,942 A | 12/1997 | Palti |
| 5,702,407 A | 12/1997 | Kaji |
| 5,713,371 A | 2/1998 | Sherman et al. |
| 5,713,896 A | 2/1998 | Nardella |
| 5,713,942 A | 2/1998 | Stern et al. |
| 5,715,832 A | 2/1998 | Koblish et al. |
| 5,716,389 A | 2/1998 | Walinsky et al. |
| 5,720,743 A | 2/1998 | Bischof et al. |
| 5,746,750 A | 5/1998 | Prestel et al. |
| 5,747,637 A | 5/1998 | Shinoda et al. |
| 5,749,879 A | 5/1998 | Middleman et al. |
| 5,759,154 A | 6/1998 | Hoyns |
| 5,766,135 A | 6/1998 | Terwilliger |
| 5,776,129 A | 7/1998 | Mersch |
| 5,792,059 A | 8/1998 | Furia et al. |
| 5,797,397 A | 8/1998 | Rosenberg |
| 5,800,378 A | 9/1998 | Edwards et al. |
| 5,817,022 A | 10/1998 | Vesely |
| 5,836,906 A | 11/1998 | Edwards |
| 5,840,033 A | 11/1998 | Takeuchi |
| 5,895,386 A | 4/1999 | Odell et al. |
| 5,895,395 A | 4/1999 | Yeung |
| 5,899,861 A | 5/1999 | Friemel et al. |
| 5,904,651 A | 5/1999 | Swanson et al. |
| 5,910,484 A | 6/1999 | Haupert, Jr. |
| 5,911,691 A | 6/1999 | Mochizuki et al. |
| 5,916,173 A | 6/1999 | Kirsner |
| 5,921,933 A | 7/1999 | Sarkis et al. |
| 5,922,008 A | 7/1999 | Gimpelson |
| 5,941,889 A | 8/1999 | Cermak |
| 5,979,453 A | 11/1999 | Savage et al. |
| 5,980,534 A | 11/1999 | Gimpelson |
| 6,013,088 A | 1/2000 | Karavidas |
| 6,015,541 A | 1/2000 | Greff et al. |
| 6,019,724 A | 2/2000 | Gronningsaeter et al. |
| 6,032,673 A | 3/2000 | Savage et al. |
| 6,033,398 A | 3/2000 | Farley et al. |
| 6,034,477 A | 3/2000 | Peeters et al. |
| 6,035,238 A | 3/2000 | Ingle et al. |
| 6,039,693 A | 3/2000 | Seward et al. |
| 6,045,508 A | 4/2000 | Hossack et al. |
| 6,066,139 A | 5/2000 | Ryan et al. |
| 6,077,257 A | 6/2000 | Edwards et al. |
| 6,080,118 A | 6/2000 | Blythe |
| 6,096,051 A | 8/2000 | Kortenbach et al. |
| 6,106,473 A | 8/2000 | Violante et al. |
| 6,169,914 B1 | 1/2001 | Hovland et al. |
| 6,175,751 B1 | 1/2001 | Maizes |
| 6,186,947 B1 | 2/2001 | Ouchi |
| 6,210,330 B1 | 4/2001 | Tepper |
| 6,231,515 B1 | 5/2001 | Moore et al. |
| 6,254,601 B1 | 7/2001 | Burbank et al. |
| 6,261,234 B1 | 7/2001 | Lin |
| 6,280,441 B1 | 8/2001 | Ryan |
| 6,293,954 B1 | 9/2001 | Fogarty et al. |
| 6,368,340 B2 | 4/2002 | Malecki et al. |
| 6,425,867 B1 | 7/2002 | Vaezy et al. |
| 6,584,360 B2 | 6/2003 | Francischelli et al. |
| 6,635,017 B1 | 10/2003 | Moehring et al. |
| 6,905,506 B2 | 6/2005 | Burbank et al. |
| 2002/0165579 A1 | 11/2002 | Burbank et al. |
| 2002/0183771 A1 | 12/2002 | Burbank et al. |
| 2002/0188306 A1 | 12/2002 | Burbank et al. |
| 2003/0120286 A1 | 6/2003 | Burbank et al. |
| 2003/0120306 A1 | 6/2003 | Burbank et al. |
| 2003/0191391 A1 | 10/2003 | Burbank et al. |
| 2003/0216759 A1 | 11/2003 | Burbank et al. |
| 2004/0059352 A1 | 3/2004 | Burbank et al. |
| 2004/0092979 A1 | 5/2004 | Burbank et al. |
| 2004/0153105 A1 | 8/2004 | Burbank et al. |
| 2004/0158262 A1 | 8/2004 | Burbank et al. |
| 2004/0193028 A1 | 9/2004 | Burbank et al. |
| 2004/0202694 A1 | 10/2004 | Burbank et al. |

FOREIGN PATENT DOCUMENTS

| | | |
|---|---|---|
| DE | 200 22 012 U1 | 5/2001 |
| EP | 0 472 368 | 2/1992 |
| EP | 0 598 579 | 5/1994 |
| EP | 1 072 282 | 1/2001 |
| GB | 2054026 | 6/1979 |
| GB | 2 302 025 | 1/1997 |
| GB | 2 311 468 A | 1/1997 |
| SU | 1 072 859 A | 2/1984 |
| WO | WO 95/02370 | 1/1995 |
| WO | WO 95/02371 | 1/1995 |
| WO | WO 96/05776 | 2/1996 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 01/68720 | 9/2001 |
| WO | WO 01/80713 | 11/2001 |
| WO | WO 02/00192 | 1/2002 |
| WO | WO 02/39904 A1 | 5/2002 |

OTHER PUBLICATIONS

Bateman, William M.D., "Treatment of intractable menorrhagia by bilateral uterine vessel, Interruption", *Am. J. Obst. & Gynec.* 89(6):825-827 (Jul. 15, 1964).

Brigato, G. et al., "A Noninvasive Instrumental Method in Severe Postpartum Hemorrhages", *Minerva Ginecologica* 50(7-8):337-339 (1998).

Brohim, Robert M. et al., "Development of Independent Vessel Security After Ligation With Absorbable Sutures or Clips", *The American Journal of Surgery*, Mar. 1993, vol. 165, pp. 345-348.

Burbank, Fred et al., "Uterine Artery Occlusion by Embolization or Surgery for the Treatment of Fibroids: A Unifying Hypothesis-Transient Uterine Ischemia", *The Journal of the American Association of Gynecologic Laparoscopists*, Nov. 2000, vol. 7, No. 7 Supplemental, pp. S3-S49.

Fuchs, Karl, "Afibrinogenemia Treated by Ligation of Uterine Arteries", *Gynacologic* 148:407-411 (1959).

Garza Leal, J. et al., "Myoma Treatment by Transient Uterine Ischemia", *The Journal of the American Association of Gynecologic Laparoscopists* 7(3):S31 (Aug. 2000).

Hay, D.L. et al., "Hemostasis in Blood Vessels After Ligation", *Am. J. Obstet. Gynecol.*, Mar. 1989, 160:3, pp. 737-739.

Hunerbein, M. et al., "Endoscopic Ultrasound-Guided Real Time Biopsy of Peri-Intestinal Tumors", *Surgical Technology International VII*, 1998, pp. 91-95.

O'Leary, James A., M.D., "Uterine Artery Ligation in the Control of Postcesarean Hemorrhage", *The Journal of Reproductive Medicine, Inc.*, 40(3):189-193 (Mar. 1995).

O'Leary, James L., M.D. et al., "Uterine artery ligation in the control of intractable postpartum hemorrhage", *Am. J. Obst. & Gynec.* 94(7):920-924 (Apr. 1, 1966).

Ravina, J.H. et al., "Arterial Embolisation to Treat Uterine Myomata", *The Lancet*, Sep. 9, 1995, vol. 346, No. 8976, pp. 671-672.

Schaefer, C.J. et al., "Absorbable Ligating Clips", *Surg. Gynecol. Obstet.*, 1982, 154:513-516.

"Mick 200-TP Applicator Package", Mick Radio-Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostrate Gland", Bruel & Kjaer Medical Systems, Inc., advertisement.

Anatomy of the Human Body, Gray, Henry, 1985, pp. 752, 1574 and 1575; included to show the anatomy of the part of the body Applicant's invention is directed to.

International Search Report for PCT/US2005/038393, mailed Mar. 1, 2006.

Written Opinion of the International Searching Authority for PCT/US2005/038393, mailed Mar. 1, 2006.

Notification of Transmittal of International Preliminary Report on Patentability received in International application No. PCT/US05/38393.

SHORT TERM TREATMENT FOR UTERINE DISORDER

RELATED APPLICATIONS

This application claims priority from U.S. Provisional Patent Application Ser. No. 60/622,751 filed Oct. 27, 2004 which is herein incorporated by reference in its entirety.

FIELD OF THE INVENTION

The invention is generally directed to the treatment of uterine disorders by detecting and regulating blood flow through one or both of the patient's uterine arteries.

BACKGROUND OF THE INVENTION

Hysterectomy (surgical removal of the uterus) is performed on approximately 600,000 women annually in the United States. Hysterectomy is often the therapeutic choice for the treatment of uterine cancer, adenomyosis, menorrhagia, prolapse, dysfunctional uterine bleeding (abnormal menstrual bleeding that has no discrete anatomic explanation such as a tumor or growth), and muscular tumors of the uterus, known as leimyoma or uterine fibroids.

However, hysterectomy is a drastic treatment, having many undesirable characteristics. Thus, any method which can approximate the therapeutic result of a hysterectomy without removing the uterus would be a significant improvement in this field. Newer treatment methods have been developed for some diseases which may spare these women a hysterectomy.

In an article published in 1964, Bateman reported that uterine artery vessel ligation or division, achieved via infraabdominal surgery similar to hysterectomy, was effective in treating menorrhagia both with and without myomectomy. Bateman, W., M.D., "Treatment of intractable menorrhagia by bilateral uterine vessel interruption", 89 Am. J. Obstet. Gynecol. 825-827 (Harcourt Health Sciences, Jul. 15, 1964). While Bateman reported some success, this procedure involves opening the abdominal cavity, with the known attendant risks and disadvantages.

In 1995, it was demonstrated that uterine fibroids could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 346; pp. 671-672, incorporated in its entirety herein). This technique is known as "uterine artery embolization". In this technique, uterine arteries are accessed via a transvascular route from a common femoral artery into the left and right uterine arteries by means of an intravascular catheter and embolic material, such as small metallic coils, polyvinyl alcohol particulate and the like, is delivered through the catheter to the uterine arteries which quickly become occluded.

See also Burbank, Fred, M.D., et al, Uterine Artery Occlusion by Embolization or Surgery for the Treatment of Fibroids: A Unifying Hypothesis Transient Uterine Ischemia, The Journal of the American Association of Gynecologic Laparoscopists, November 2000, Vol. 7, No. 4 Supplement, pp. S3-S49. U.S. Pat. No. 6,254,601, to Fred Burbank et al, entitled "Methods for Occlusion of the Uterine Arteries", describes numerous devices and methods useful for occluding a uterine artery by penetrating the tissue of the patient to access the uterine artery. The devices and methods described in Burbank '601 have been useful in occluding a uterine artery, however there have been some difficulties encountered with their use.

The uterus has a dual (or redundant) blood supply, the primary blood supply being from the bilateral uterine arteries, and the secondary blood supply from the bilateral ovarian arteries. Consequently, when both uterine arteries are occluded, i.e. bilateral vessel occlusion, the uterus and the fibroids contained within the uterus are both deprived of their blood supply. However, as demonstrated by Ravina et al. and Burbank et al., the ischemic effects on the fibroid is greater than the effect on the uterus. In most instances, the fibroid withers and ceases to cause clinical symptoms.

However, many physicians do not possess the training or equipment necessary to perform catheter-based uterine artery embolization under radiologic direction. Accordingly, there are substantially fewer uterine artery embolizations performed, worldwide, each year than hysterectomies for symptomatic uterine fibroids and other uterine disorders.

Recently, fibroid treatment procedures have been described wherein the uterine arteries are temporarily occluded by an intravaginal device which is clamped or otherwise pressed against a tissue bundle with the patient's uterine artery being within the bundle. Pressure on the tissue occludes the underlying uterine artery causing thrombus to form in the occluded artery. While these procedures have shown much promise, they typically take about six hours for completely effective treatment, which means the patient must be under observation and frequently sedated during the period.

What is needed, therefore, are intravaginal devices and procedures for using such devices which can be easily used by physicians with limited training to occlude blood flow in a female patient's uterine arteries and which reduces the period the patient's uterine arteries must be clamped.

SUMMARY OF THE INVENTION

The invention is directed to a device and method for treating a female patient's uterine disorder by occluding one or both of the patient's uterine artery. The treatment is suitable for uterine disorders such as uterine fibroids, dysfunctional uterine bleeding (DUB), and post partum hemorrhage (PPH) by reducing or terminating blood flow through one or both of the female patient's uterine arteries.

The treatment embodying features of the invention basically involves occluding one or both of the patient's uterine arteries with an intravaginal device to form a thrombus within the occluded artery or arteries and administering an agent which will prolong the occlusion of the artery or arteries after removal of the occluding device or initiate or accelerate fibroid cell apoptosis (programmed cell death). The agent may act to retard or prevent lysis of the thrombus or may act to reduce uterine blood flow which can retard lysis. The agent can be an anti-fibrinolytic agent administered to the patient to retard or prevent lysis of the thrombus formed by the uterine artery occlusion for essentially the duration of the treatment. By maintaining an effective amount of the anti-fibrinolytic agent within the patient's blood stream, the lysis of the thrombus within the uterine arteries after the occluding device (e.g. clamp) is removed is retarded or prevented. This allows the occluding device to be removed earlier thereby shortening the clamping period. Moreover, the uterine artery occlusion after occluding device removal can be extended by maintaining an effective level of anti-fibrinolytic agent within the patient.

After the uterine arteries have been occluded for a sufficient time, the administration of the anti-fibrinolytic agent can be terminated so that lysis of the thrombus is initiated by the normal lysis cycle and blood flow through the arteries can resume. Administering the anti-fibrinolytic agent allows for blood stasis to occur within the uterus and eliminates or retards the clot lysis cycle which can minimize the effect of the treatment. The stasis in the uterus initiates a clotting cascade and by minimizing the competitive lysis cycle a quicker treatment can be delivered. The clot is maintained after removal of the occlusion system by the continued administration of the anti-fibrinolytic agent.

The preferred anti-fibrinolytic agent is a plasminogen binding agent which is believed to bind to plasminogen and prevents tissue plasminogen activator (tPa) and urine plasminogen activator (uPa) from binding with plasminogen. When tPa and the uPa bind with the plasminogen to generate plasmin which solubilizes (lyses) fibrin clots and also degrades various proteins including fibrinogen and coagulation factors. The presently preferred plasminogen binding agent is tranexamic acid (TA). Typically, the TA is delivered to the patient intravenously. An alternative plasminogen binding agent is ethamsylate, but this agent is not as effective as tranexamic acid and is required in much larger doses. Other anti-fibrinolytic agents include acexamic acid, aminocaproic acid and aprotinin.

Another agent which can enchance the effects of the clamping of the uterine arteries is misoprostol. An effective level of Misoprostol can reduce blood flow in the uterus and reduce the amount of fibrinolytic agent reaching the thrombus thereby extending the period in which the thrombus will remain in place. Additionally, other agents capable of reducing uterine artery blood flow can be administered.

Agents which stimulate production of Bax and Bak proteins can be administered as well to augment fibroid tissue necrosis. Bax and Bak are proteins which promote apoptosis or programmed cell death. Bax and Bak protein levels are elevated in ischemic fibroid tissue. The proto-oncogene Bcl-2 is found in abundance in the cells of a fibroid, compared to normal myometrial cells. Bcl-2 is believed to play an important role in the growth of tumors. An agent which inhibits the protein expression of Bcl-2 can be used to treat fibroids. Furthermore, agents which produce effects similar to those created by inhibition Bcl-2 or stimulation of Bax or Bak, can be administered to aid in treatment of fibroids.

An intravaginal device embodying features of the invention has a pair of clamping members Each of the clamping members have an elongated handle which is configured in part to extend out of the patient during the procedure and a clamping jaw with pressure applying surfaces for uterine artery occlusion. The distal ends of the jaws are configured to engage the patient's vaginal fornix on opposite sides of the patient's uterine cervix and to apply pressure to the patient's vaginal fornix to occlude the underlying uterine arteries.

The elongated handles of the occluding members are preferably pivotally mounted so that manipulation of the proximal shaft sections of the occluding members, which extend out of the patient during the procedure, will adjust the spacing between the pressure applying surfaces on the distal ends of the jaws.

The intravaginal device should be stabilized with respect to the patient's uterus by a positioning member or shaft such as a tenaculum to facilitate a more effective application of pressure by the pressure applying member to the vaginal fornix to ensure occlusion of the patient's uterine artery.

In one embodiment of the invention, one or more blood flow sensors, preferably based on Doppler ultrasound, are provided on at least one of the pressure applying surfaces to aid in the location of the patient's uterine arteries, and to monitor the occlusion thereof. When the pressure applying surfaces of the jaws are pressed against the wall of the vaginal fornix, the vaginal wall is distended so as to more closely approach a uterine artery. Applying tension to the uterine cervix by the tenaculum or tenaculum type device or implement, including forceps, suction devices, and the like, help to reduce the distance from the patient's vaginal fornix to the patient's uterine artery.

A method for occluding a patient's uterine arteries which embodies features of the invention includes advancing the intravaginal device through the patient's vaginal canal, preferably slidably mounted on a previously deployed tenaculum or tenaculum-like device. The stabilizing shaft of the tenaculum-like device, which is partially deployed within the patient's uterine cervix, guides the intravaginal device so that the clamping jaws of the device are disposed adjacent to the sides of the patient's cervix. The positions of the pressure applying surfaces of the clamping jaws are adjusted utilizing the blood flow sensors to ensure that the pressure applying surfaces on the clamping jaws are properly positioned with respect to the uterine arteries for effective occlusion thereof.

The invention allows for the non-surgical location and occlusion of blood vessels such as the uterine artery, providing effective therapeutic treatment. Importantly, the present invention allows for the occlusion of a female patient's uterine artery without the need for radiographic equipment or for extensive training in the use of radiographic techniques. The devices and methods are simple and readily used for treating uterine fibroids, dysfunctional uterine bleeding (DUB), adenomyosis, post-partum hemorrhage, and other uterine disorders. The mechanical occlusion portion of the treatment period is shortened considerably by the administration of an anti-fibrinolytic agent to the patient to maintain the occluding thrombus within the patient's uterine arteries. The shortened treatment times allows the patient to be more mobile, simplifies the treatment and reduces the patient monitoring and care needed. Furthermore, reduced artery clamping periods reduces the trauma to the patient's cervix and vaginal mucosa. The shorter treatment periods also increases the number of patient's which can be treated over a given period.

These and other advantages will become more apparent from the following detailed description when taken in conjunction with the accompanying exemplary drawings.

DETAILED DESCRIPTION OF THE INVENTION

The treatment embodying features of the invention basically involves occluding one or both of the patient's uterine arteries with a device to form thrombus within the occluded artery or arteries and administering an agent to the patient which will allow for occlusion of the artery or arteries to be prolonged after removal of the device. The agent may act to prevent lysis of the thrombus or may act to reduce uterine blood flow.

Figure 1:
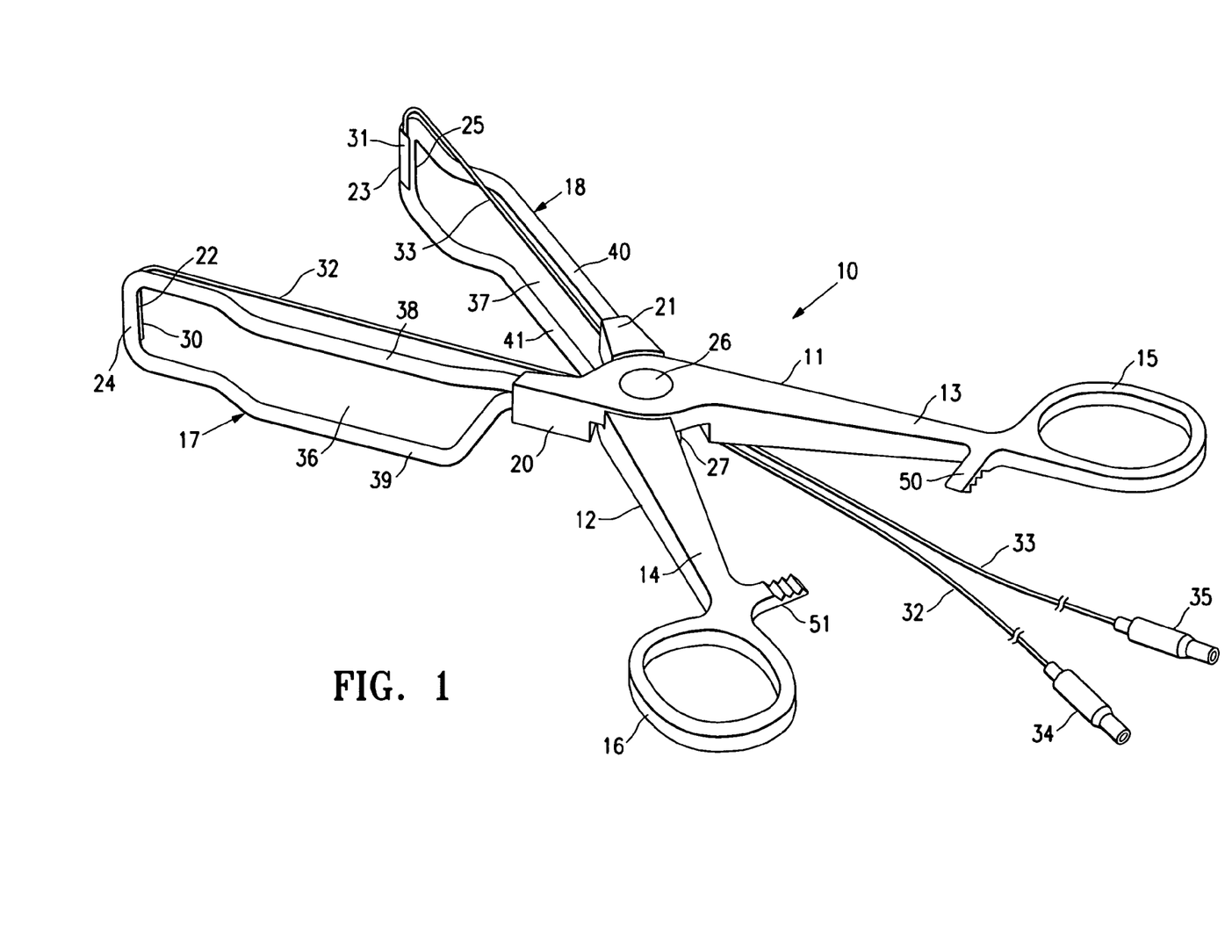
FIG. 1 is a perspective view of a uterine artery intravaginal device which embodies features of the invention.
Figures 2, 3:
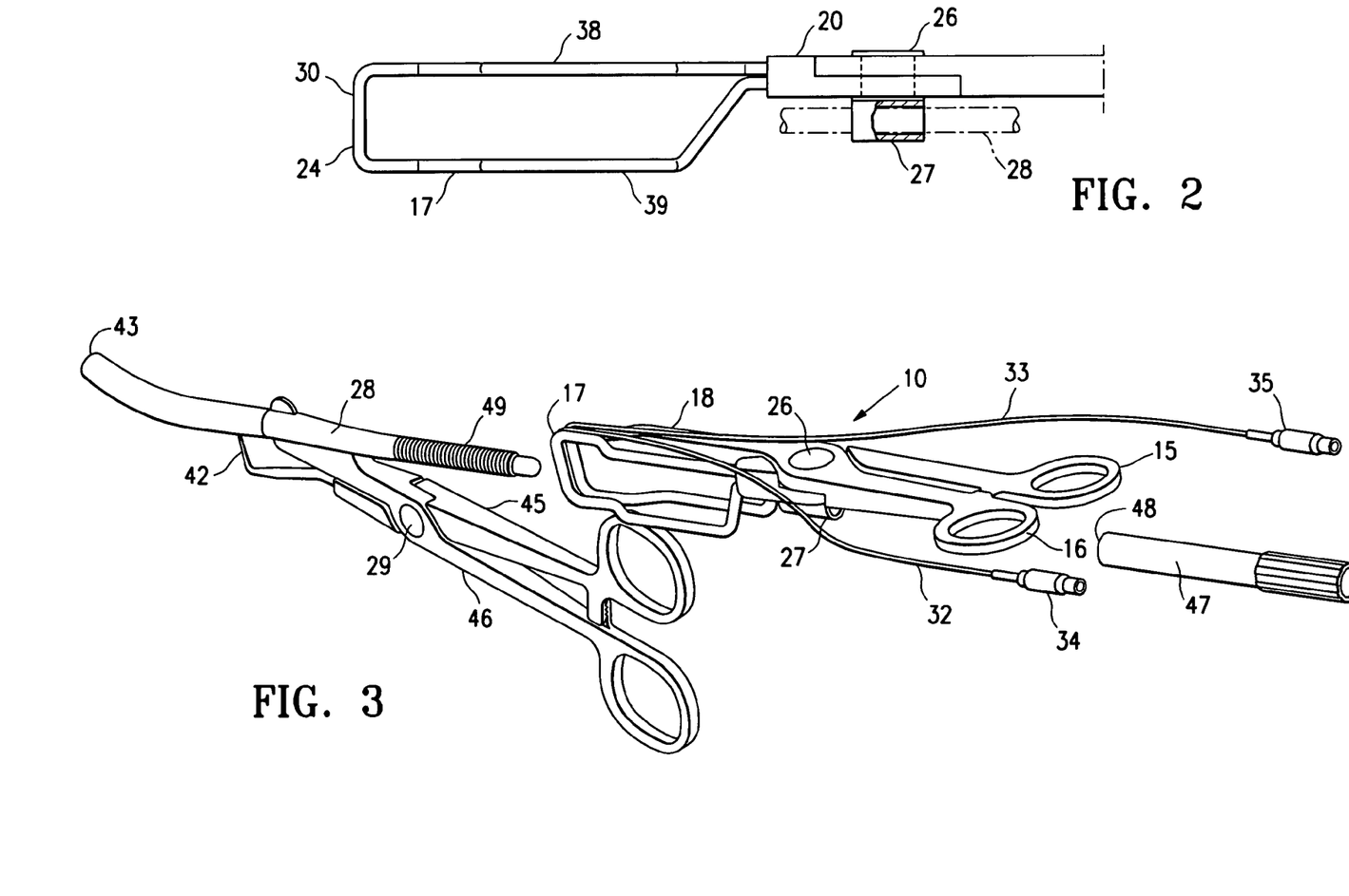
FIG. 2 is a side view of the distal portion of the uterine artery intravaginal device shown in FIG. 1.
FIG. 3 is an exploded perspective view of a system including the intravaginal device shown in FIG. 1 and a tenaculum-type device configured to slidably receive the intravaginal device.

FIGS. 1 and 2 illustrate a relatively non-invasive intravaginal device 10 embodying features of the invention. The device 10 includes a pair of elongated clamping members 11 and 12, each of which has an elongated handle 13 and 14 respectively with finger grips 15 and 16 on the proximal ends of the handles. Clamping jaws 17 and 18 are secured to the distal ends 20 and 21 respectively of handles 13 and 14. The clamping jaws 17 and 18 are provided with pressure-applying surfaces 22 and 23 respectively on the distal ends 24 and 25 of the clamping elements. The handles 13 and 14 are pivotally connected at pivot point 26 to facilitate the opening and closing of the clamping jaws 17 and 18. A shoe slider 27 (shown in FIG. 2) is provided on the under side of the intravaginal device 10 for mounting the intravaginal device to the shaft 28 of a tenaculum like device 29 (as shown in FIG. 3) to guide the intravaginal device 10 to the patient's uterine cervix.

Blood flow sensors 30 and 31 are secured to the pressure applying surfaces 22 and 23 respectively. Conductors 32 and 33 are electrically connected by their distal ends to the sensors 30 and 31 and extend proximally. The proximal ends of the conductors 32 and 33 have adaptors 34 and 35 to be operatively connected to power source (not shown) with an audio or video display to convert the sensed blood flow signal from the sensors to actuate an audible report or a video display representing the blood flow sensed.

The clamping jaws 17 and 18 shown in FIGS. 1 and 2 are open, paddle-like members which have opposed tissue receiving recesses 36 and 37 proximal to the distal ends 24 and 25 of the jaws 17 and 18 which are defined in part by longitudinally oriented top side element 38 and bottom side element 39 for recess 36 and top side element 40 and bottom side element 41 for recess 37. In one embodiment, the longitudinally oriented top side elements 38, 40 are spaced from the respective longitudinally oriented bottom side elements 39, 41 a distance of about 1-20 mm. In one embodiment, the longitudinally oriented top side elements 38, 40 are spaced from the respective longitudinally oriented bottom side elements 39, 41 a distance of about 5-10 mm. The proximal ends of the side elements 38-41 are secured to the distal ends 24 and 25 of handles 13 and 14. The top side elements 36 and 38 of the clamping elements are essentially in line with the distal ends 24 and 25 of the handles 13 and 14. The bottom side elements 37 and 39 are spaced away from the top elements and preferably extend below the shoe slider 27 so that the distal ends 24 and 25 of the clamping elements 17 and 18 are equally disposed above and below the shaft 28 of tenaculum-like device 29 (Shown in FIGS. 2 and 3) to properly engage the patients vaginal fornix and to apply pressure to the underlying uterine arteries to occlude these arteries.

FIG. 3 is an exploded view of the system embodying features of the invention including the intravaginal device 10 described above and the tenaculum-like device 29. The tenaculum-like device has a pointed distal tip 42 configured to engage tissue of the patient's uterine cervix. The distal tip 43 of the shaft 28 is flared as shown to maintain the tip within the patient's uterine cervix 44 during the procedure. Handles 45 and 46 allow movement between the tip 42 and the shaft 28 to manipulate the patient's uterine cervix. Sheath 47 is provided with internal threads (not shown) within its distal end 48 which are configured to engage the threads 49 on the shaft 28 to prevent the withdrawal of the intravaginal device during the procedure. Details of the tenaculum device 29 are found in co-pending application Ser. No. 10/300,420, filed on Nov. 19, 2002, and co-pending application Ser. No. 10/716,329, filed on Nov. 18, 2003, both of which are assigned to the present assignee.

Figure 4:
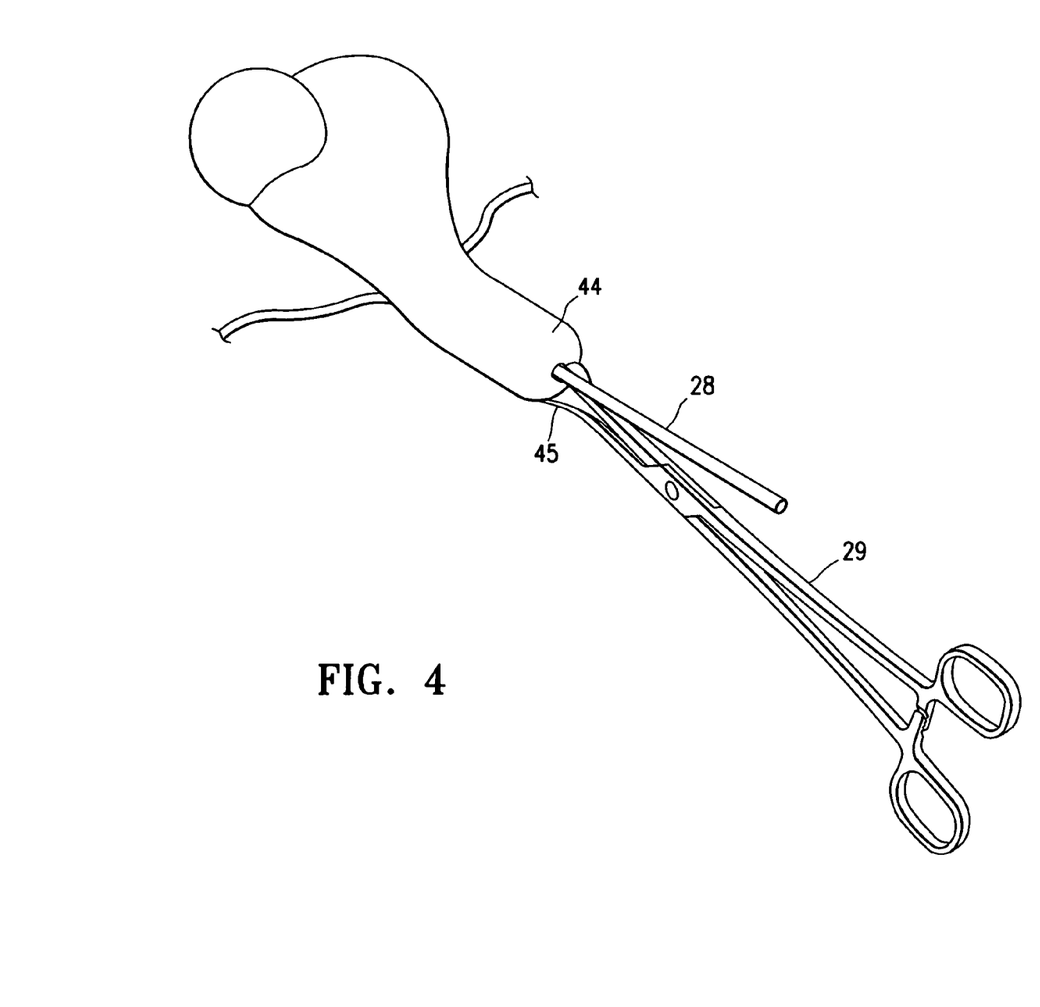
FIG. 4 is a perspective view of a tenaculum-type device mounted within a patient's uterine cervix.

FIG. 4 illustrates the deployment of the tenaculum like device 29 within the patient's vaginal canal (not shown) with the shaft 28 of the tenaculum-like device inserted into the patient's uterine cervix 44. The handle 45 of the tenaculum-like device 29 has a sharp distal tip 42 for engaging cervical tissue to be able to manipulate the patient's uterine cervix during the procedure when positioning the intravaginal device 10 about the patient's uterine cervix 44. Handle 46 is secured to the mid-point of the shaft 28.

Figure 5:
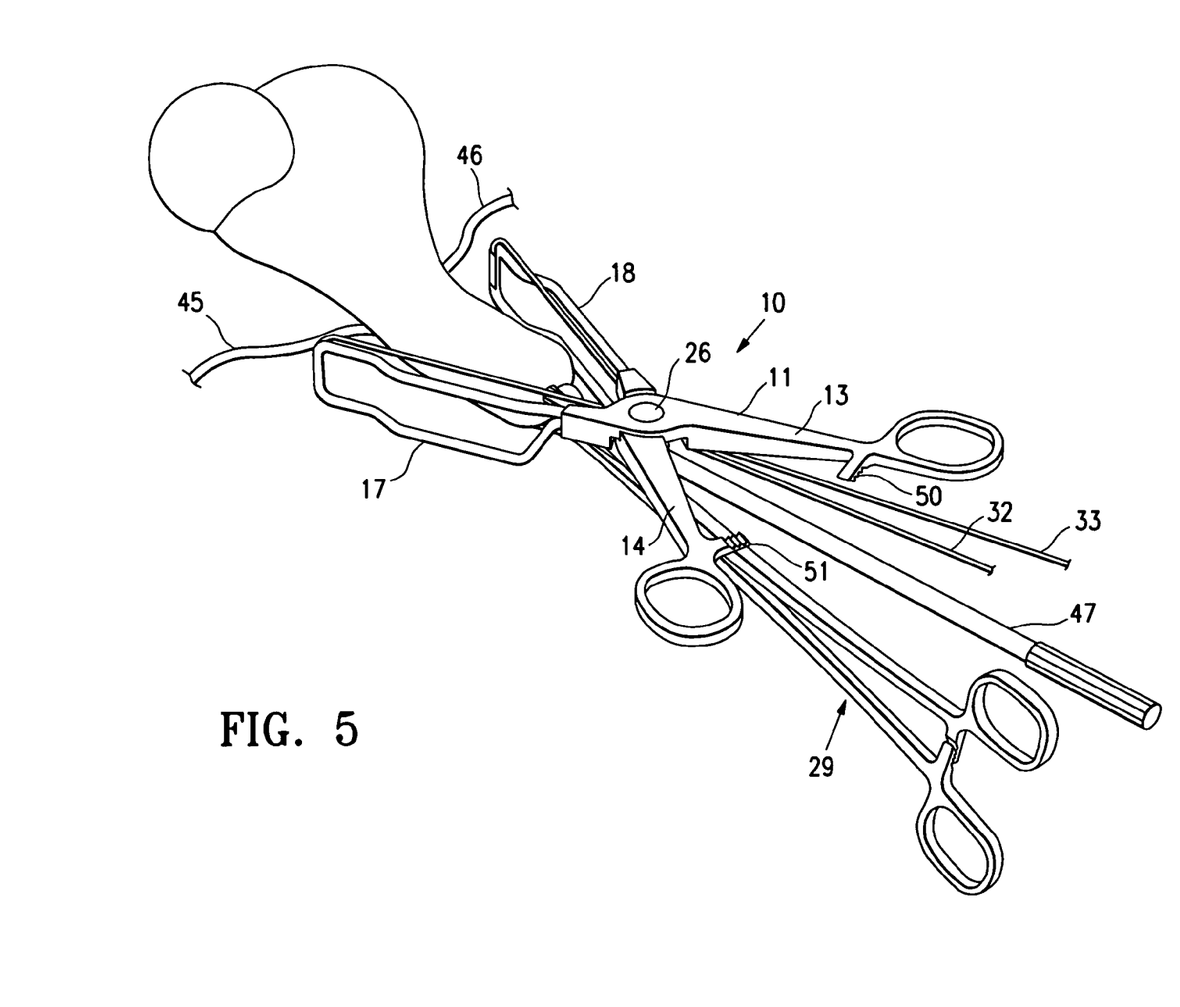
FIG. 5 is an perspective view of the intravaginal device shown in FIG. 1 mounted on the shaft of the tenaculum-like device shown in FIG. 3.
Figure 6:
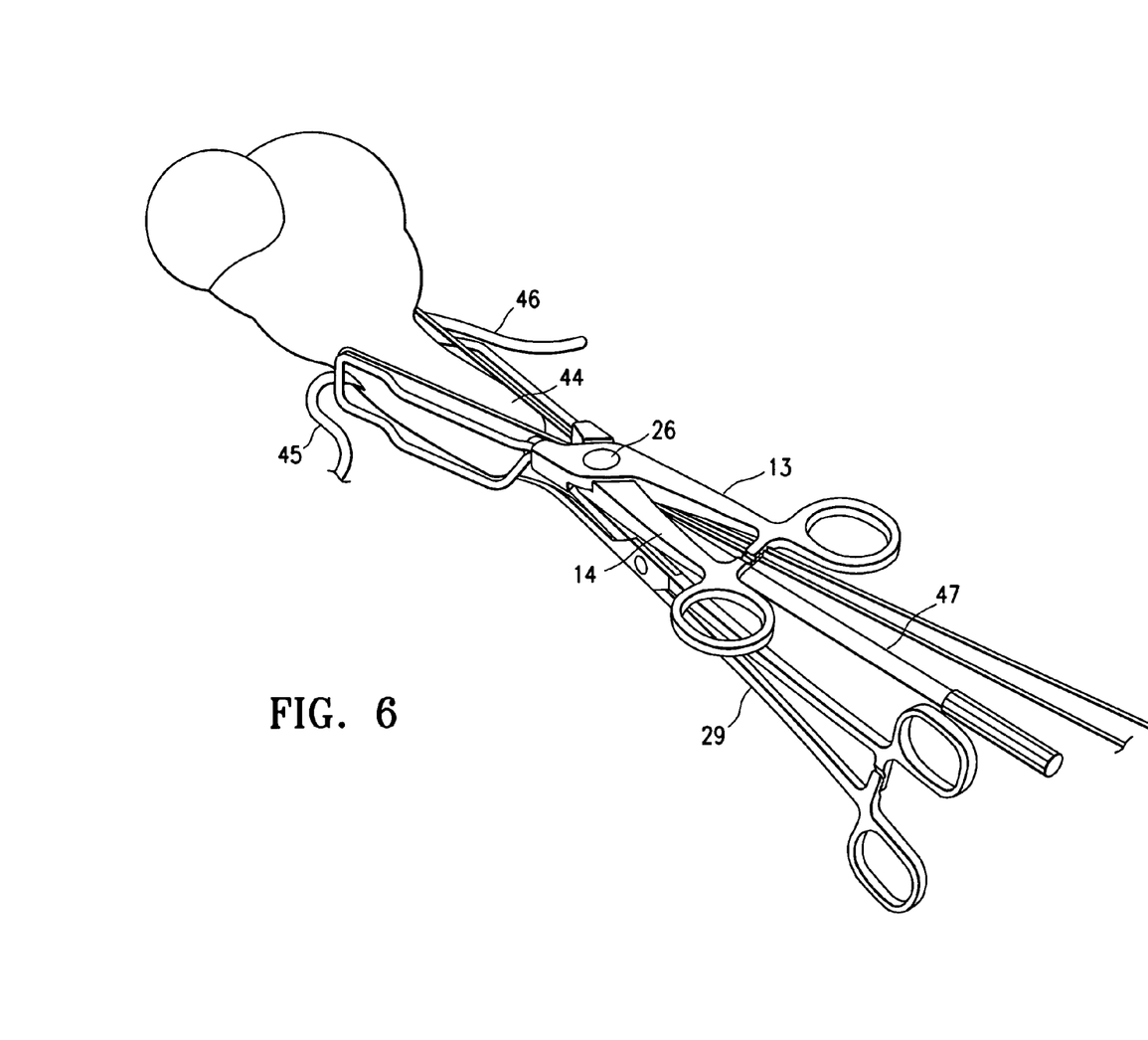
FIG. 6 is a perspective view of the intravaginal device mounted on the shaft of the tenaculum-like device shown in FIG. 4 with the pressure applying surfaces of the intravaginal device pressing against the patient's uterine arteries.

As shown in FIG. 5, the intravaginal device 10 is mounted onto the shaft 28 of the tenaculum-like device 29 with the shaft 28 slidably extending within the shoe slide 27. The intravaginal device 10 is advanced within the patient's vaginal canal (not shown) over the shaft 28 of the tenaculum-like device 29 until the open jaws 17 and 18 of the device 10 extend over the end of the patient's uterine cervix as shown in FIG. 5. The distal ends 24 and 25 are urged against the patient's vaginal fornix on both sides of the cervix 44. The position of the distal ends 24 and 25 is adjusted to facilitate use of the blood flow sensors 30 and 31 on the pressure applying surfaces 22 and 23 to detect the underlying uterine arteries 45 and 46. The operator squeezes the finger grips 15 and 16 on the proximal ends of handles 13 and 14 to press the pressure applying surfaces against the patient's vaginal fornix to occlude the underlying uterine arteries as shown in FIG. 6. The ratchet locks 50 and 51 on the handles 13 and 14 adjacent the finger grips 15 and 16 engage to lock the handles 13 and 14 together with the pressure applying surfaces 22 and 23 of the jaws 17 and 18 pressed against the vaginal fornix with the underlying uterine arteries 45 and 46 occluded. The blood flow sensors 30 and 31 can be employed to monitor the blood flow through the uterine arteries 45 and 46 and to detect blood flow termination when the arteries are occluded.

The blood flow sensors 30 and 31 are preferably Doppler ultrasonic sensing systems to allow the operator to more easily guide the clamping jaws 17 and 18 to the location of the patient's target uterine arteries 45 and 46. The blood flow sensor is preferably mounted to the face of a tissue-contacting, pressure applying surface of the jaws of the intravaginal device and is preferably oriented perpendicularly to the pressure applying surface. Other orientations can be employed. In one embodiment, the blood flow sensor is a Doppler crystal that has a direction of view away from the pressure applying surface. Ultrasound energy useful for sensing a location of a blood vessel or of blood flow in a blood vessel has a frequency of less than about 20 MegaHertz (MHz), such as between about 5 MHz and about 19 MHz, and preferably between about 6 MHz and about 10 MHz. In commercially available Doppler sensors, the frequency is typically about 8 MHz. For sensors based on electromagnetic energy useful for sensing a location of a blood vessel or of blood flow in a blood vessel, the EM energy should have a wavelength of about 500 nanometers (nm) to about 2000 nm, preferably about 700 nm to about 1000 nm.

Suitable Doppler ultrasonic systems include the MedaSonics® CardioBeat® Blood Flow Doppler with Integrated Speaker (Cooper Surgical, Inc., Trumbull, Conn.). Other commercially available suitable Doppler ultrasound sensors are the Koven model ES 100× MiniDop VRP-8 probe (St. Louis, Mo.) and the DWL/Neuro Scan Medical Systems' Multi-Dop B+ system (Sterling, Va.).

While not shown in the drawings, the pressure applying surface of the occluding elements can be provided with a serrated or other tissue-grasping surface which is configured to engage and hold onto tissue when the pressure applying surfaces are pressed into tissue of the patient's vaginal fornix.

The uterine arteries in human females are located adjacent the vaginal mucosa at a location within a few centimeters of the vaginal fornix. As a result, for accessing and occluding a uterine artery from within the patient's vaginal canal, the dimensions of a vagina determine what size intravaginal device is suitable, taking into consideration that the intravaginal device should readily reach the vaginal fornix and be manually operated from outside of a patient's body. For example, a intravaginal device can be between about 6 inch to about 12 inches (15.2-30.5 mm) in length for most applications.

The clamping jaws 17 and 18 are locked position about 0.5 to about 3 hours, preferably about 1 to about 2 hours for effective occluding of the patient's uterine arteries. During or shortly after the occlusion of the patient's uterine arteries, thrombus forms in the arteries. An agent can be administered to the patient in addition to the clamping to enhance the effects of the occluded artery and decrease the time necessary for the device to remain in place.

The agent can be an anti-fibrinolytic agent, which retards or prevents lysis of the thrombus formed by the uterine artery occlusion for essentially the duration of the treatment. By maintaining an effective amount of the anti-fibrinolytic agent within the patient's blood stream, the lysis of thrombus within the uterine arteries is retarded or prevented, so the thrombus formation is accelerated, reducing the clamping period. Moreover, the uterine artery occlusion can be extended by maintaining an effective level of anti-fibrinolytic agent within the patient after the clamping pressure by the intravaginal device has been released.

After the uterine arteries have been occluded for a sufficient time, the administration of the anti-fibrinolytic agent can be terminated so that lysis of the thrombus is initiated by the normal lysis cycle and blood flow through the arteries can resume. By administering the anti-fibrinolytic agent allows for blood stasis to occur within the uterus and but eliminates or retards the clot lysis cycle which can minimize the effect of the treatment. The stasis in the uterus initiates a clotting cascade and by minimizing the competitive lysis cycle a shorter treatment period can be obtained. The clot is maintained after removal of the occlusion system by maintaining an effective level of the anti-fibrinolytic agent within the patient.

If the thrombus is not lysed, the thrombus effectively blocks blood flow through the artery, so the clamping jaw is no longer needed and it can be removed. Preferably, the anti-fibrinolytic agent has been administered to the patient and an effective level of the agent is developed within the patient's blood before the jaws of the intravaginal device are clamped together to occlude the patient's uterine arteries.

The preferred anti-fibrinolytic agent is a plasminogen binding agent which is believed to bind to plasminogen and prevents tissue plasminogen activator (tPa) and urine plasminogen activator (uPa) from binding with plasminogen. When tPa and the uPa bind with the plasminogen to generate plasmin which solubilizes (lyses) fibrin clots and also degrades various proteins including fibrinogen and coagulation factors.

The presently preferred plasminogen binding agent is tranexamic acid (TA). Typically, the TA is delivered to the patient intravenously. Initially, the patient's are given 10 mg TA/kg of patient weight over a thirty minute period, followed by a constant drip at 1 mg TA/kg of body weight for the duration of the treatment time. An alternative plasminogen binding agent is ethamsylate, but this agent is not as effective as tranexamic acid and is required in much larger doses. Other anti-fibrinolytic agents include acexamic acid, aminocaproic acid and aprotinin.

By maintaining an anti-fibrinolytic agent within the patient's blood, clot formation from the artery occlusion is accelerated because the clot lysis cycle is retarded or eliminated allowing for reduced occlusion times. When an anti-fibrinolytic agent is used to accelerate the uterine artery occlusion, the uterine arteries should be occluded for a period of about 0.5 to about 3 hours, usually about 1 to about 2 hours for effective treatment of the uterine disorder. The uterine artery occlusion can be extended after the clamping members of the intravaginal device have been released by the continued administration of the anti-fibrinolytic agents to the patient. By retarding or preventing lysis of the thrombus within the patient's uterine arteries and uterus, the arteries remain occluded even though the pressure applied by the jaws of the intravaginal device have been released. The occluding thrombus is maintained within the patient's uterus and uterine arteries to provide a total artery occlusion time period of about 1 to about 48 hours, preferably about 1 to about 24 hours for effective treatments of the patient's uterine disorder. Typically, the total occlusion time will be less than 6 hours At the end of the treatment, administration of the anti-fibrinolytic agents is terminated. Typically lysis of the thrombus within the occluded uterine arteries begins about a half an hour after the administration of the anti-fibrinolytic agent has been terminated. Within about 24 hours the thrombus has been completely lysed and full blood flow resumes.

Another agent which can enchance the effects of the clamping of the uterine arteries is misoprostol. An effective level of Misoprostol can reduce blood flow in the uterus and reduce the amount of fibrinolytic agent reaching the thrombus thereby extending the period in which the thrombus will remain in place. Additionally, other agents capable of reducing uterine artery blood flow can be administered.

Agents which stimulate production of Bax and Bak proteins can be administered as well to augment fibroid tissue necrosis. Bax and Bak are proteins which promote apoptosis or programmed cell death. Bax and Bak protein levels are elevated in ischemic fibroid tissue. The proto-oncogene Bcl-2 is found in abundance in the cells of a fibroid, compared to normal myometrial cells. Bcl-2 is believed to play an important role in the growth of tumors. An agent which inhibits the protein expression of Bcl-2 can be used to treat fibroids. Furthermore, agents which produce effects similar to those created by inhibition Bcl-2 or stimulation of Bax or Bak, can be administered to aid in treatment of fibroids.

The uterine artery intravaginal devices embodying features of the invention can be made from any suitable material or combination of materials, including metals such as stainless steel, cobalt-chromium alloys, cobalt-chromium-nickel alloys, chromium-cobalt-molybdenum alloys and superelastic alloys such as nickel-titanium alloys having a stable austenite phase at body temperature, high strength plastics, ceramics, and other materials known in the art to be suitable for the uses contemplated herein. Biocompatible polymers such as polycarbonate, polysulfone, polyester, polyacetal and a variety of fluoropolymers can be suitable for a variety of embodiments of the invention. The intravaginal devices and systems embodying features of the invention can be designed for single use (disposable) or can be sterilizable and capable of multiple use.

While particular forms of the invention have been illustrated and described, it will be apparent that various modifications can be made to the invention and that individual features shown in one embodiment can be combined with any or all the features of another embodiment described herein. The intravaginal device described herein is a presently preferred embodiment, but other uterine artery intravaginal devices can be utilized. For example, other suitable intravaginal devices are described in co-pending application Ser. No. 10/107,810, filed on Mar. 28, 2002, Ser. No. 10/107,800, filed on Mar. 28, 2002, Ser. No. 10/430,880, Ser. No. 10/721,857, filed on Nov. 25, 2003 and Ser. No. 10/718,222, filed on Nov. 20, 2003, all of which have been assigned to the present assignee. Accordingly, the invention is not to be limited to the specific embodiments illustrated and should be defined by the scope of the appended claims as broadly as the prior art will permit. Terms such as "element", "member", "device", "component", "section", "portion", "steps", "means" and words of similar import, if used in the appended claims, shall not be construed as invoking the provisions of 35 U.S.C. §112(6) unless the claims expressly use the term "means" followed by a particular function without reciting specific structure or use the term "step" followed by a particular function without reciting specific action. All patents and patent applications cited herein are hereby incorporated in their entireties by reference.

What is claimed is:

1. An intravaginal device for treating a female patient's uterine disorder by occluding at least one of the patient's uterine arteries, comprising:
  a. a first clamping member which has
    i. an elongated handle with a proximal handle portion configured to extend out of the patient during treatment and be manipulated by an operator, which has a distal handle portion having a pivot point and which is configured to rotate in a plane about the pivot point, and
    ii. a paddle-shaped jaw which is secured to the distal handle portion, which has a distal end with a pressure applying surface, which has an inside tissue receiving recess proximal to the pressure applying surface with upper and lower longitudinally oriented sides proximal to the distal end defining in part the tissue receiving recess, with the upper longitudinally oriented side in line with the distal handle portion and the lower longitudinally oriented side spaced away from the upper longitudinally oriented side; and
  b. a second clamping member which has
    i. an elongated handle with a proximal handle portion configured to extend out of the patient during treatment and be manipulated by an operator along with the proximal handle portion of the first clamping member, which has a distal handle portion having a pivot point pivotally secured to the pivot point of the handle of the first clamping member and which is configured to rotate in the plane about the pivot point, and
    ii. a second paddle-shaped jaw secured to the distal handle portion of the second clamping member having a distal end with a pressure applying surface opposed to the pressure applying surface of the first clamping member, a tissue receiving recess proximal to the pressure applying surface extending away from the tissue receiving recess of the first clamping member, a pair of longitudinally oriented sides, with an upper one of the longitudinally oriented sides in the rotational plane of the distal handle portion of the second clamping member and a lower one of the longitudinally oriented sides spaced away from the upper one of the longitudinally oriented sides, wherein the device is mounted to a tenaculum-like device having an elongated shaft to guide the device to the patient's uterine cervix, wherein the device has a shoe slider located below the pivot point for mounting the device to the tenaculum-like device, wherein the upper longitudinally oriented sides of the first and second paddle-shaped jaws extend above the shoe slider and the lower longitudinally oriented sides of the first and second paddle-shaped jaws extend below the shoe slider, and wherein the shoe slider is positioned between the upper longitudinally oriented sides and the lower longitudinally oriented sides of the paddle-shaped jaws so that the distal ends of the paddle-shaped jaws are equally disposed above and below the elongated shaft of the tenaculum-like device to properly engage a patient's vaginal fornix and to apply pressure to the patient's underlying uterine arteries to occlude the arteries.

2. The intravaginal device of claim 1 wherein each of the proximal shaft sections of the clamping members include a grip configured to receive an operator's finger.

3. The intravaginal device of claim 1 wherein at least one of the clamping members has a blood flow sensor on its distal tip for detecting the location of the patient's uterine artery.

4. The intravaginal device of claim 1 wherein the blood flow sensor is a Doppler crystal.

5. The intravaginal device of claim 4 wherein the Doppler crystal is mounted in the pressure applying surface of the distal tip.

6. The intravaginal device of claim 5 wherein the Doppler crystal has a direction of view away from the pressure applying surface.

7. The intravaginal device of claim 1 wherein the pair of longitudinally oriented sides of the clamping members are spaced apart a distance of about 1 to about 20 mm.

8. The intravaginal device of claim 7 wherein the pair of longitudinally oriented sides of the clamping members are spaced apart a distance of about 5 to about 10 mm.

9. The intravaginal device of claim 1 wherein the distal end of the paddle-shaped jaw of the first clamping member and the distal end of the paddle-shaped jaw of the second clamping member are configured to engage the patient's vaginal fornix on opposite sides of the patient's uterine cervix.

10. The intravaginal device of claim 1, wherein the tenaculum-like device comprises the elongated shaft having a distal tip that is flared for maintaining the distal tip within a patient's uterine cervix, and a proximal end having external threads.

11. The intravaginal device of claim 10, further comprising a sheath having a distal end with internal threads adapted to engage the external threads at the proximal end of the elongated shaft of the tenaculum-like device to prevent the withdrawal of the intravaginal device during a procedure.

12. An intravaginal device for occluding uterine arteries comprising:
  a first clamping member including
    a first elongated handle having a proximal handle portion and a distal handle portion;
    a paddle-shaped jaw secured to the distal handle portion, the paddle-shaped jaw having a distal end with a pressure applying surface and upper and lower longitudinally extending sides proximal to the distal end defining a tissue receiving recess located proximal to the pressure applying surface, wherein the upper longitudinally extending side is in alignment with the distal handle portion and the lower longitudinally extending side is spaced away from the upper longitudinally extending side;
  a second clamping member including
    a second elongated handle having a second proximal handle portion and a second distal handle portion;
    a second paddle-shaped jaw secured to the second distal handle portion, the second paddle-shaped jaw having a second distal end with a second pressure applying surface and second upper and lower longitudinally extending sides proximal to the second distal end defining a second tissue receiving recess located proximal to the second pressure applying surface, wherein the second upper longitudinally extending side is in alignment with the second distal handle portion and the second lower longitudinally extending side is spaced away from the second upper longitudinally extending side;

a pivot point pivotally connecting the first and second elongated handles together for enabling the first and second upper longitudinally extending sides of the respective first and second paddle-shaped jaws to rotate toward and away from one another within a first plane of rotation that is aligned with the first and second distal handle portions;

a shoe slider located below the pivot point; and a tenaculum-like device having an elongated shaft insertible into the shoe slider for stabilizing the intravaginal device, wherein the shoe slider is located between the first and second upper longitudinally extending sides and the first and second lower longitudinally extending sides so that the distal ends of the first and second paddle-like jaws are equally disposed above and below the elongated shaft of the tenaculum-like device to properly engage a patient's vaginal fornix and to apply pressure to the patient's underlying uterine arteries to occlude the arteries.

13. The intravaginal device of claim 12, wherein the first and second lower longitudinally extending sides are rotatable toward and away from one another within a second plane of rotation that is spaced from the first plane of rotation.

* * * * *